United States Patent
Huisman et al.

(10) Patent No.: US 6,942,839 B2
(45) Date of Patent: Sep. 13, 2005

(54) PROCESS FOR THE PRODUCTION OF LIQUID HYDROCARBONS

(75) Inventors: Hans Michiel Huisman, Amsterdam (NL); Koen Willem De Leeuw, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/931,490

(22) Filed: Sep. 1, 2004

(65) Prior Publication Data

US 2005/0032919 A1 Feb. 10, 2005

Related U.S. Application Data

(62) Division of application No. 10/276,615, filed as application No. PCT/EP01/05716 on May 17, 2001, now Pat. No. 6,806,297.

(30) Foreign Application Priority Data

May 19, 2000 (EP) .......................................... 00304264

(51) Int. Cl.$^7$ .............................. B01J 10/00; B01J 8/04
(52) U.S. Cl. ...................... 422/188; 422/189; 422/190; 422/194; 422/198
(58) Field of Search .............................. 422/188, 189, 422/190, 194, 198

(56) References Cited

U.S. PATENT DOCUMENTS

| | | | |
|---|---|---|---|
| 4,833,170 A | 5/1989 | Agee | |
| 5,545,674 A | 8/1996 | Behrmann et al. | |
| 6,114,400 A | * 9/2000 | Nataraj et al. | 518/715 |
| 6,265,453 B1 | * 7/2001 | Kennedy | 518/703 |

FOREIGN PATENT DOCUMENTS

| | | | |
|---|---|---|---|
| EP | 0645344 | 3/1985 | ............. C01B/3/38 |
| EP | 576 096 | 12/1993 | ............. C01B/3/38 |
| EP | 0629578 | 12/1994 | ............. C01B/3/40 |
| EP | 0656317 | 6/1995 | ............. C01B/3/40 |
| EP | 0773906 | 5/1997 | ............. C01B/3/38 |
| WO | 91/15446 | 10/1991 | ........... C07C/27/06 |
| WO | 93/06041 | 4/1993 | ........... C01B/21/00 |
| WO | 94/21512 | 9/1994 | ........... B63B/35/44 |
| WO | 97/12118 | 4/1997 | ........... E21B/43/01 |
| WO | 97/30011 | 8/1997 | ............. C07C/7/06 |
| WO | 98/01514 | 1/1998 | ............. C10G/2/00 |
| WO | 99/34917 | 7/1999 | ............. B01J/23/75 |

OTHER PUBLICATIONS

Oil and Gas Journal, Sep. 6, 1971, pp. 86–90.

* cited by examiner

*Primary Examiner*—J. Parsa

(57) ABSTRACT

A process for producing normally liquid hydrocarbon products from a hydrocarbonaceous feedstock, especially from normally gaseous hydrocarbon feed, having the following steps: (a) partial oxidation of the normally gaseous hydrocarbon feed at elevated pressure using air or oxygen enriched air as oxidant, to obtain a syngas mixture having hydrogen, carbon monoxide and nitrogen; (b) converting hydrogen and carbon monoxide obtained in step (a) into a normally liquid hydrocarbon product and a normally gaseous hydrocarbon product; (c) separating from the reaction mixture obtained in step (b) an off-gas mixture having nitrogen, normally gaseous hydrocarbon product, and unconverted hydrogen, carbon monoxide and normally gaseous hydrocarbon feed, insofar as such unconverted components are present; (d) combusting at least a part of the off-gas mixture in a steam raising apparatus, producing steam of an elevated pressure; and (e) expanding the steam produced in step (d) for compressing the air or oxygen enriched air and/or the normally gaseous hydrocarbon feed used in step (a); and a plant having equipment in a line-up suitable for carrying out the process.

2 Claims, No Drawings

PROCESS FOR THE PRODUCTION OF LIQUID HYDROCARBONS

This is a Divisional of application Ser. No. 10/276,615, filed Nov. 18, 2002, now U.S. Pat. No. 6,806,297, which is a 371 of PCT/EP01/05716 filed May 17, 2001.

FIELD OF THE INVENTION

The present invention relates to a process for the production of liquid hydrocarbons from a gaseous hydrocarbon feed, especially the optimisation of an integrated, low-cost process for the production of normally liquid hydrocarbons from natural gas or especially associated gas, at remote locations or at offshore locations.

BACKGROUND OF THE INVENTION

Many publications (cf. for example WO-94/21512, WO-97/12118, WO-91/15446 and U.S. Pat. No. 4,833,170) describe processes for the conversion of (gaseous) hydrocarbon feed, such as methane, natural gas and/or associated gas, into liquid products, especially methanol and liquid hydrocarbons, particularly paraffinic hydrocarbons. Such conversion processes may be operated at remote locations (e.g. in desserts, tropical rain-forests) and/or offshore locations, where no direct use of the gas is possible, due to the absence of large populations and industries. Transportation of the gas to populated and industrial areas, e.g. through a pipeline or in the form of liquefied natural gas, requires extremely high capital expenditure or is simply not practical. This holds even more in the case of relatively small gas production fields and/or relatively small gas production rates. Re-injection of gas into the production field will add to the costs of the oil production, and may, in the case of associated gas, result in undesired effects on the crude oil production. Burning of associated gas has become undesired in view of depletion of hydrocarbon sources and air pollution.

Gas found together with crude oil is known as associated gas, whereas gas found separate from crude oil is known as non-associated gas. Associated gas may be found as "solution gas" dissolved within the crude oil, and/or as "gas cap gas" adjacent to the main layer of crude oil. Associated gas is usually much richer in the larger hydrocarbon molecules (ethane, propane, butane) than non-associated gas.

Especially in view of the fact that the above-mentioned conversion processes may be operated at remote locations or at locations where limited space is available there is an incentive to place special emphasis on such factors as energy and cost efficiency, compactness and complexity of the process or the plant in which the process is carried out. From the references given above, however, no optimally integrated, efficient, low-cost process scheme is available.

WO-98/01514 discloses a process in which gaseous hydrocarbon feed is converted with air into syngas which, in turn, is converted into liquid hydrocarbon product in a Fischer-Tropsch synthesis step. A substantial amount of the heat generated in the process is recovered and re-used in the process. Further, an off-gas mixture which is co-produced in the Fischer-Tropsch synthesis is used to fuel a gas turbine which, in turn, is used to power the compressor needed for compressing the air used in the process. The off-gas mixture in question comprises unconverted syngas, methane by-product from the Fischer-Tropsch synthesis, and nitrogen originating from the air used. The use of air as the oxidant in the conversion of the gaseous hydrocarbon obviates the need of a production unit of an oxygen rich oxidant. However, the nitrogen present in the air acts in the process as a diluent gas, necessitating handling larger quantities of gas at a higher total pressure, which requires more compression capacity.

A further disadvantageous aspect of the use of air is that the said off-gas mixture is diluted with nitrogen which causes that it has a low heating value. The heating value is especially low when the syngas production and the Fischer-Tropsch synthesis are operated efficiently, so that the content of combustible materials in the off-gas mixture is further decreased. In the light of the process of WO-98/01514 this will represent a problem when the heating value is so low that the off-gas mixture is unsuitable for use as a gas turbine fuel.

SUMMARY OF THE INVENTION

It has now been found that when the off-gas mixture is unsuitable for use as a gas turbine fuel, sufficient energy for operating the compressors, and even for operating the whole process, can be recovered from the off-gas mixture by burning the off-gas mixture for the production of steam and using the steam as the source of shaft power and/or electrical power. This finding leads to an integrated, highly efficient, low-cost process with low capital and space requirements for the production of normally liquid hydrocarbons from normally gaseous hydrocarbons. Further, there is no need for the importation of additional fuel or other sources of energy for operating the process. The process has a high carbon efficiency, which means that a high proportion of the carbon present in the hydrocarbon feed is present in the normally liquid hydrocarbon products.

DETAILED DESCRIPTION OF THE INVENTION

The present finding may be applied especially when associated gas is the feedstock, which, after separation from the crude oil, is usually available at low pressure or even at ambient pressure only. The present finding may also be applied when the feed is gas from low pressure gas fields or largely depleted gas fields, having only a low remaining pressure. In a preferred embodiment, the process may be carried out in a compact, relatively light weight plant, making it very suitable for use on a platform or a barge, or in a dismountable plant.

A major advantage of the present finding is that relatively simple and cheap processes and apparatus can be used. Further, an optimal use of feedstock and energy is obtained. In a preferred embodiment an optimum carbon conversion (gas into syncrude, minimal carbon dioxide emission), is obtained. In addition, the normally liquid hydrocarbons produced may be mixed with crude oil and transported together.

The present invention thus provides a process for producing normally liquid hydrocarbon products from a hydrocarbonaceous feedstock, especially from a normally gaseous hydrocarbon feed, which comprises the following steps:
(a) partial oxidation of the normally gaseous hydrocarbon feed at elevated pressure using air or oxygen enriched air as oxidant, to obtain a syngas mixture comprising hydrogen, carbon monoxide and nitrogen;
(b) converting hydrogen and carbon monoxide obtained in step (a) into a normally liquid hydrocarbon product and a normally gaseous hydrocarbon product;
(c) separating from the reaction mixture obtained in step (b) an off-gas mixture comprising nitrogen, normally gaseous hydrocarbon product, and unconverted hydrogen, carbon monoxide and normally gaseous hydrocarbon feed, insofar as such unconverted components are present;

(d) combusting at least a part of the off-gas mixture in a steam raising apparatus, producing steam of an elevated pressure; and (e) expanding the steam produced in step (d) for compressing the air or oxygen enriched air and/or the normally gaseous hydrocarbon feed used in step (a).

The invention also relates to a plant comprising equipment in a line-up suitable for carrying out the process of this invention.

The normally gaseous hydrocarbon feed is suitably methane, natural gas, associated gas or a mixture of $C_{1-4}$ hydrocarbons, preferably associated gas. The $C_{1-4}$ hydrocarbons or mixtures thereof are gaseous at temperatures between 5 and 30° C. at 1 bara (i.e. bar absolute), especially at 20° C. at 1 bara. The normally gaseous hydrocarbon feed comprises mainly, i.e. more than 80% v, especially more than 90% v, $C_{1-4}$ hydrocarbons. The normally gaseous hydrocarbon feed comprises especially at least 60% v methane, preferably at least 75% v, more preferably at least 90% v. Very suitably natural gas or associated gas is used, especially associated gas at a remote location or at an offshore location. In some cases the natural gas or the associated gas comprises in addition carbon dioxide and/or nitrogen, e.g. in amounts up to 15% v or even up to 25% v of each of these compounds on the normally gaseous hydrocarbon feed.

The normally liquid hydrocarbons mentioned in the present description are suitably $C_{4-24}$ hydrocarbons, especially $C_{5-20}$ hydrocarbons, more especially $C_{6-16}$ hydrocarbons, or mixtures thereof. These hydrocarbons or mixtures thereof are liquid at temperatures between 5 and 30° C. at 1 bara, especially at 20° C. at 1 bara, and usually are paraffinic of nature, although considerable amounts of olefins and/or oxygenates may be present. The normally liquid hydrocarbons may comprise up to 20% w, preferably up to 10% w, of either olefins or oxygenated compounds. Depending on the catalyst and the process conditions used, also normally solid hydrocarbons may be obtained. These normally solid hydrocarbons may be formed in the Fischer-Tropsch reaction in amounts up to 85% w based on total hydrocarbons formed, usually between 50 and 75% w.

The normally gaseous hydrocarbon product comprises mainly, i.e. more than 80% v, especially more than 90% v, $C_{1-4}$ hydrocarbons. These hydrocarbons or mixtures thereof are gaseous at temperatures between 5 and 30° C. at 1 bara (i.e. bar absolute), especially at 20° C. at 1 bara, and usually are paraffinic of nature, although considerable amounts of olefins and/or oxygenates may be present. The normally gaseous hydrocarbon product comprises especially at least 30% v methane, preferably at least 40% v, more preferably at least 50% v. The normally gaseous hydrocarbon product may comprise up to 20% w, preferably up to 10% w, of either olefins or oxygenated compounds.

Suitably, any sulphur in the normally gaseous hydrocarbon feed is removed, for example, in an absorption tower a sulphur binding agent, such as iron oxide or zinc oxide.

The partial oxidation of the normally gaseous hydrocarbon feed, producing the syngas mixture can take place according to various established processes. These processes include the Shell Gasification Process. A comprehensive survey of this process can be found in the Oil and Gas Journal, Sep. 6, 1971, pp. 86–90. The reaction is suitably carried out at a temperature between 800 and 2000° C. and a pressure between 4 and 80 bara.

Oxygen for use in step (a) is sourced from air or from oxygen enriched air. The oxygen enriched air gas comprises suitably up to 70% v oxygen, preferably up to 60% v, in particular in the range of from 25 to 40% v. Oxygen enriched air may be produced by cryogenic techniques, but preferably it is produced by a process which is based on separation by means of a membrane, such as disclosed in WO-93/06041. The use of oxygen enriched air is not a preferred option. Preferably air is employed in step (a).

Very suitable processes for partial oxidation are catalytic partial oxidation processes, especially as described in EP-A-576096, EP-A-629578, EP-A-645344, EP-A-656317 and EP-A-773906. In the catalytic partial oxidation processes a catalyst bed may be applied. Suitable structures of the catalyst bed are monolith structures, especially ceramic foams, but also metal based structures may be used. The monolithic structures may comprise inorganic materials of high temperature resistance, selected from compounds of elements of Groups IIa, IIIa, IVa, IIIb, IVb and the lanthanide group of the Periodic Table of the Elements. Preferably the monolithic structure is zirconia based, especially stabilised zirconia. Suitable active metals for the catalytic partial oxidation process are rhodium, platinum, palladium, osmium, iridium and ruthenium, and mixtures thereof. Preferably, rhodium and/or iridium is used.

The temperature applied in the catalytic partial oxidation is usually between 700 and 1300° C., suitably between 800 and 1200° C., preferably between 850 and 1050° C., and the pressure is usually between 4 and 80 bara, suitably between 10 and 50 bara, preferably between 15 and 40 bara.

The GHSV is suitably in the range of 50,000 to 100,000,000 Nl/l/h, preferably 500,000 to 50,000,000 Nl/l/h, especially 1,000,000 to 20,000,000 Nl/l/h. The term "GHSV" is well known in the art, and relates to the gas per hour space velocity, i.e. the volume of synthesis gas in Nl (i.e. at the standard temperature of 0° C. and the standard pressure of 1 bara (100,000 Pa)) which is contacted in one hour with one liter of catalyst particles, i.e. excluding inter-particular void spaces. In the case of a fixed bed catalyst, the GHSV is usually expressed as per liter of catalyst bed, i.e. including interparticular void space. In that case a GHSV of 1.6 Nl/l/h on catalyst particles corresponds frequently with 1.0 Nl/l/h on catalyst bed.

To adjust the $H_2/CO$ ratio of the syngas mixture, carbon dioxide and/or steam may be introduced into the partial oxidation process. As a suitable steam source, water which is co-produced in step (b) may be used. As a suitable carbon dioxide source, carbon dioxide from the effluent gasses of the combustion of step (d) may be used. The $H_2/CO$ ratio of the syngas mixture is suitably between 1.5 and 2.3, preferably between 1.8 and 2.1.

If desired, a small amount of hydrogen may be made separately, for example, by steam reforming of gaseous normally hydrocarbon feed, preferably in combination with the water shift reaction, and added to the syngas mixture. Any carbon monoxide and carbon dioxide produced together with the hydrogen may be used as additional feed in step (b), or it may be recycled to step (a) to increase the carbon efficiency. Alternatively, it may be combusted in step (d), together with or in admixture with the normally gaseous hydrocarbon product.

To keep the process as simple as possible, separate hydrogen manufacture will usually not be a preferred option. Likewise, it is not a preferred option to remove any nitrogen from the syngas mixture, or from any other normally gaseous product mixture described in this patent document.

In another embodiment the $H_2/CO$ ratio of the syngas mixture may be decreased by removal of hydrogen from the syngas mixture. This can be done by conventional techniques, such as pressure swing adsorption or cryogenic processes. A preferred option is a separation based on membrane technology. In the case that hydrogen is removed from the syngas mixture it may be preferred to apply a two-stage conversion in step (b). The hydrogen is then mixed with the gaseous products of the first stage, and together introduced in the second stage. The $C_5$+ selectivity (i.e. the selectivity to hydrocarbons containing 5 or more carbon atoms, expressed as a weight percentage of the total hydrocarbon product) can be improved in this line-up. A portion of the hydrogen may be used in an optional, additional hydrocracking step in which especially the heavier fraction of the hydrocarbons produced in step (b) is cracked, as set out hereinafter.

Typically the normally gaseous hydrocarbon feed fed to the partial oxidation of step (a) is completely converted therein. Frequently, the percentage of hydrocarbon feed which is converted amounts to 50–99% w and more frequently 80–98% w, in particular 85–96% w.

It is preferred that the heat generated in the partial oxidation is recovered for re-use in the process. For example, the syngas mixture obtained in step (a) may be cooled, typically to a temperature between 100 and 500° C., suitably between 150 and 450° C., preferably between 200 and 400° C. Preferably, the cooling is effected in a steam raising apparatus, such as a boiler, with simultaneous generation of steam typically of an elevated pressure. Further cooling to temperatures between 30 and 130° C., preferably between 40 and 100° C., may be accomplished in a conventional heat exchanger, especially in a tubular heat exchanger for example against cooling water or against the feed led to the reactor, or in an air cooler against air.

To remove any impurities from the syngas mixture, a guard bed may be used. Especially to remove all traces of HCN and/or $NH_3$ specific types of active coal may be used. Trace amounts of sulphur may be removed by an absorption process using iron oxide and/or zinc oxide.

In step (b) the syngas mixture is converted into the normally liquid hydrocarbons and normally gaseous hydrocarbons. Suitably at least 70% v of the syngas (i.e. the portion of the syngas mixture consisting of hydrogen and carbon monoxide) fed to step (b), is converted. Preferably all the syngas fed to step (b) is converted, but frequently 80 to 99% v, more frequently 90 to 98% v is converted. Typically all of the syngas obtained in step (a) is fed into step (b) and more typically all of the syngas mixture obtained in step (a) is fed into step (b).

The conversion of step (b) of hydrogen and carbon monoxide into hydrocarbons is well known in the art and it is herein referred to by the usual term "Fischer-Tropsch synthesis". Catalysts for use in the Fischer-Tropsch synthesis frequently comprise, as the catalytically active component, a metal from Group VIII of the Periodic Table of Elements. Particular catalytically active metals include ruthenium, iron, cobalt and nickel. Cobalt is a preferred catalytically active metal. Typically, at least a part of the catalytically active metal is present in metallic form.

The catalytically active metal is preferably supported on a porous carrier. The porous carrier may be selected from any of the refractory metal oxides or silicates or combinations thereof known in the art. Particular examples of preferred porous carriers include silica, alumina, titania, zirconia, ceria, gallia and mixtures thereof, especially silica and titania.

The amount of catalytically active metal present in the catalyst is preferably in the range of from 3 to 75% w, more preferably from 10 to 50% w, especially from 15 to 40% w, relative to the weight of the catalyst.

If desired, the catalyst may also comprise one or more metals or metal oxides as promoters. Suitable metal oxide promoters may be oxides of elements selected from Groups IIA, IIIB, IVB, VB and VIB of the Periodic Table of Elements, and the actinides and lanthanides. In particular, oxides of magnesium, calcium, strontium, barium, scandium, yttrium. lanthanum, cerium, titanium, zirconium, hafnium, thorium, uranium, vanadium, chromium and manganese are most suitable promoters. Particularly preferred metal oxide promoters for the catalyst used in the present invention are manganese and zirconium oxide. Suitable metal promoters may be selected from Groups VIIB and VIII of the Periodic Table. Rhenium and Group VIII noble metals are particularly suitable, with platinum and palladium being especially preferred. The amount of promoter present in the catalyst is suitably in the range of from 0.01 to 50% w, preferably 0.1 to 30% w, more preferably 1 to 15% w, relative to the weight of the catalyst.

The catalytically active metal and the promoter, if present, may be deposited on the carrier material by any suitable treatment, such as impregnation, kneading and extrusion. After deposition of the metal and, if appropriate, the promoter on the carrier material, the loaded carrier is typically subjected to calcination at a temperature generally in the range of from 350 to 750° C., preferably in the range of from 450 to 550° C. After calcination, the resulting catalyst may be activated by contacting the catalyst with hydrogen or a hydrogen-containing gas, typically at a temperature in the range of from 200 to 350° C. Particular forms of catalyst are shell catalysts, in which the catalytically active metal and the promoter, if present, are positioned in the outer layer of relatively coarse catalyst particles, e.g. extrudates (cf. e.g. U.S. Pat. No. 5,545,674 and the references cited therein), and catalysts which are present in the form of a powder, e.g. a spray dried powder, suitable for forming a slurry in the liquid reaction medium of the Fischer-Tropsch synthesis (cf. e.g. WO-99/34917).

Preferably a catalyst is used which comprises cobalt on a titania carrier, because such a catalyst is highly efficient in the Fischer-Tropsch synthesis in that it provides a high conversion of syngas combined with a high $C_5$+ selectivity, when compared with other catalysts, thus a low production of the gaseous hydrocarbon products. Preferably, the catalyst contains a further metal selected from manganese, vanadium, zirconium, rhenium, scandium, platinum and ruthenium. Preferably the further metal is manganese or vanadium, in particular manganese.

The Fischer-Tropsch synthesis may conveniently and advantageously be operated in a single pass mode ("once through") devoid of any recycle streams, thus allowing the process to be comparatively simple and relatively low cost. The process may be carried out in one or more reactors, either parallel or in series. In the case of small hydrocarbon feedstock streams, the preference will be to use only one reactor. Slurry bubble reactors, ebulliating bubble reactors and fixed bed reactors may be used. In order to minimise the production of gaseous hydrocarbon product, it is preferred to apply fixed bed reactor in combination with a shell type catalyst, or a reactor in combination with a powdery catalyst which is present as a slurry in the liquid reaction medium.

The Fischer-Tropsch synthesis may be performed under conventional conditions known in the art. Typically, the temperature is in the range of from 100 to 450° C., preferably from 150 to 350° C., more preferably from 180 to 270° C. Typically, the total pressures is in the range of from 1 to 200 bara, more preferably from 20 to 100 bara. The GHSV may be chosen within wide ranges and is typically in the range from 400 to 10000 Nl/l/h, for example from 400 to 4000 Nl/l/h.

It is preferred that the heat generated in the Fischer-Tropsch synthesis is recovered for re-use in the process. For example, the Fischer-Tropsch reaction mixture may be cooled with simultaneous generation of steam typically of an elevated pressure. This may be done outside the reactor in which the Fischer-Tropsch synthesis is carried out, for example in a conventional heat exchanger, or inside the reactor, for example by employing a multi-tubular reactor or by means of an internal cooling coil. Typically the Fischer-Tropsch reaction mixture may finally be cooled to a temperature between 40 and 130° C., preferably between 50 and 100° C., by means of a conventional heat exchanger, especially in a tubular heat exchanger for example against cooling water or against the feed led to the reactor, or in an air cooler against air.

The product of step (b), i.e. the product of the Fischer-Tropsch synthesis, is separated in step (c) into the off-gas mixture and a fraction comprising the normally liquid hydrocarbon products and, suitably, a fraction comprising the water which is co-produced in the Fischer-Tropsch synthesis. This separation may involve distillation and phase separation and it may be carried out using conventional equipment, for example a distillation column or a gas/liquid separator and optionally a liquid/liquid separator. The off-gas mixture comprises nitrogen, the normally gaseous hydrocarbon product, and unconverted hydrogen, carbon monoxide and normally gaseous hydrocarbon feed, if any of such unconverted components is present. Besides nitrogen, the off-gas mixture may comprise further non-combustible components such as carbon dioxide and inert gasses such as helium.

The pressure of the off-gas mixture is substantially the same as the pressure prevailing in the Fischer-Tropsch synthesis reactor used in step (b). If the pressure is above 1 bara, it is advantageous to expand the off-gas mixture, preferably in a turbine using its mechanical energy for compression purposes. It is preferred to use the mechanical energy of the off-gas mixture for compression of the syngas mixture prior to being fed to step (b). This effects that the Fischer-Tropsch synthesis of step (b) is performed at a relatively high pressure which leads to a better efficiency of the Fischer-Tropsch synthesis, in particular a higher conversion rate, while the partial oxidation of step (a) is performed at a relatively low pressure, at which the partial oxidation is more efficient, in terms of a better conversion level. Preferably the pressure increase of the syngas mixture amounts to at least 5 bar, in particular 10 to 50 bar, more in particular 15 to 40 bar.

In step (d), at least a part of the off-gas mixture, preferably at least 90% w, in particular all of the off-gas mixture, is combusted in a steam raising apparatus, generating steam of an elevated pressure. Preferably the off-gas mixture as fed to the steam raising apparatus is slightly above ambient pressure, typically in the range of 1.01 to 5 bara, more typically 2 to 4 bara.

The steam raising apparatus may be conventional equipment, such as a furnace equipped with heating coils, a boiler or a superheater. The pressure of the steam generated may be at least 2 bara. Preferably, steam of various pressures is generated simultaneously, for example, a low pressure steam, a medium pressure steam and a high pressure steam. The low pressure steam has a pressure of in the range of 2 to 8 bara, preferably in the range of 3 to 5 bara. The medium pressure steam has a pressure of in the range of 8 to 40 bara, preferably in the range of 10 to 30 bara. The high pressure steam has a pressure of in the range of 40 to 100 bara, preferably in the range of 50 to 80 bara. Preferably, for its efficient use in step (e), the steam produced is superheated steam. Typically the degree of superheating is at least 5° C. For practical reasons the degree of superheating is at most 100° C. Typically the degree of superheating is in the range of from 20 to 80° C.

Customarily, the heating value of a gas is expressed quantitatively by its "lower heating value". For easy combustion of the off-gas mixture in the conventional steam raising apparatus, it is preferred that the off-gas mixture has a composition such that its lower heating value is in the range of from 3 to 15 MJ/Nm$^3$ ("Nm$^3$" refers to the gas volume at 0° C., 1 bara). Preferably, the lower heating value of the off-gas is in the range of 3.5 to 11 MJ/Nm$^3$, more preferably in the range of 4 to 6 MJ/Nm$^3$. The lower heating value of the off-gas mixture can be determined experimentally or, if the composition of the off-gas mixture is known, it can be calculated by adding up the weighted contributions of the lower heating value of the individual components. The lower heating value of the relevant compounds are known to the skilled person.

In a preferred embodiment of the process the heat of combustion recovered in step (d) is used together with the heat of reaction recovered in step (a) and/or the heat of reaction recovered in step (b) for producing steam. For example, superheated high pressure steam having a pressure in the range of 60 to 65 bara may be produced by heating water to form steam using the heat of reaction recovered in step (a), followed by superheating the steam using the heat of combustion of the off-gas mixture. Alternatively, or preferably simultaneously, superheated medium pressure steam having a pressure in the range of 15 to 25 bara may be produced by heating water using the heat of combustion of the off-gas mixture, which steam is then combined with steam of equal pressure produced in the Fischer-Tropsch synthesis reactor of step (b), and subsequently superheated using the heat of combustion of the off-gas mixture. The various steps which involve heating using the heat of combustion of the off-gas mixture may be done simultaneously in a single furnace in which the off-gas mixture is combusted, by using a plurality of heating coils.

In accordance with this invention, at least a part of the steam produced is used for compressing the air or oxygen enriched air and/or the normally gaseous hydrocarbon feed. In first embodiment the steam is employed as a source of shaft power by using for the compression a compressor which is driven by a steam turbine. For example, high pressure steam of 60 to 65 bara, preferably superheated steam of that pressure, may be employed in the steam turbine for compressing the air or oxygen enriched air used in step (a). Alternatively, or preferably simultaneously, medium pressure steam of 15 to 25 bara, preferably superheated steam of that pressure, may be employed in another steam turbine which drives a compressor compressing the normally gaseous hydrocarbon feed used in step (a). In a second, less preferred embodiment the steam is employed as a source of electrical power by using for the compression a compressor which is driven electrically and the electrical power needed is generated using the power of a steam turbine which is driven be steam generated in step (e).

A further quantity of steam may be used for generating power which is used elsewhere in the process. In particular, it may be used for generating electricity, which is used for driving any electrical equipment used in the process, other than the electrically driven compressors mentioned hereinbefore (if any), such as pumps, air blowers, and other. Sometimes there is a surplus of energy, which may be applied outside the process.

The normally liquid hydrocarbon product as obtained from the step (b) may be transported in liquid form or mixed with any stream of crude oil without creating problems as to solidification and or crystallisation of the mixture. It is observed in this respect that in step (b) heavy hydrocarbons products, such as $C_{18-200}$ hydrocarbons, in particular $C_{20-100}$ hydrocarbons, may be coproduced which show a tendency to solidify as waxy materials, in which case the normally liquid hydrocarbon product becomes more difficult in its handling.

If this is the case, but also for other reasons, at least part of the hydrocarbon product may be subjected to a catalytic hydrocracking, which is known per se in the art. The catalytic hydrocracking is carried out by contacting the normally liquid hydrocarbon product at elevated temperature and pressure and in the presence of hydrogen with a catalyst containing one or more metals having hydrogenation activity, and supported on a carrier. Suitable hydrocracking catalysts include catalysts comprising metals selected from Groups VIB and VIII of the Periodic Table of Elements. Preferably, the hydrocracking catalysts contain one or more noble metals from group VIII. Preferred noble metals are platinum, palladium, rhodium, ruthenium, iridium and osmium. Most preferred catalysts for use in the hydrocracking stage are those comprising platinum. To keep the process as simple as possible, the application of a additional catalytic hydrocracking step will usually not be a preferred option.

The amount of catalytically active metal present in the hydrocracking catalyst may vary within wide limits and is typically in the range of from 0.05 to 5% w, relative to the weight of the catalyst. Suitable conditions for the catalytic hydrocracking are known in the art. Typically, the hydrocracking is effected at a temperature in the range of from about 175 to 400° C. Typical hydrogen partial pressures applied in the hydrocracking process are in the range of from 10 to 250 bara.

The catalytic hydrocracking may be carried out before the separation of step (c), but preferably it is carried out after the separation of step (c). Additional normally gaseous hydrocarbon products (i.e. hydrocarbon products or a mixture thereof which are gaseous at temperatures between 5 and 30° C. at 1 bara, especially at 20° C. at 1 bara) may be formed during the catalytic hydrocracking. Any-off gas of the catalytic hydrocracking, comprising any unconverted hydrogen and the additional normally gaseous hydrocarbon product formed, may be separated from the catalytic hydrocracking reaction product, and added to and/or combusted with the off-gas mixture in step (d).

It is an advantage of this invention that the process can be carried out without the need of having available gas which has a high heating value for fueling a gas turbine for power generation, so that it can advantageously be used as feedstock in the process for the conversion into normally liquid hydrocarbon product. Thus, the normally gaseous hydrocarbon feed can be used completely for conversion purposes. Further, the off-gas mixture may be of a low heating value, which means that the partial oxidation and the Fischer-Tropsch synthesis may be operated at a high efficiency so that the process is performed with a high carbon efficiency.

There is no need to import energy for operating the process from sources outside the process and/or to install a gas turbine for power generation. In the case that energy would be imported from a source outside the process, for example for a reason of convenience, the quantity of energy imported will be less than 50%, preferably less than 25%, more preferably less than 10% relative to the energy needed for operating the process, i.e. the total energy needed to drive the energy consuming equipment employed in the process, such as heat generating equipment, compressors, pumps, air blowers, and other.

The hydrocarbonaceous feed is preferably a normally gaseous hydrocarbon feed, but may also be a solid hydrocarbon feed, e.g. coal, brown coal, peat or organic waste.

The process may be carried out at a remote location and/or offshore, for example on a vessel or platform.

What is claimed is:

1. A plant comprising:
   (a) a reactor for partially oxidating a normally gaseous hydrocarbon feed at elevated pressure using air or oxygen enriched air as oxidant, to obtain a syngas mixture comprising hydrogen, carbon monoxide and nitrogen;
   (b) a Fischer-Tropsch synthesis reactor for converting hydrogen and carbon monoxide obtained in step (a) into a normally liquid hydrocarbon product and a normally gaseous hydrocarbon product;
   (c) a separator for separating from the reaction mixture obtained in step (b) an off-gas mixture comprising nitrogen, normally gaseous hydrocarbon product, and unconverted hydrogen, carbon monoxide and normally gaseous hydrocarbon feed, insofar as such unconverted components are present;
   (d) a combustor for combusting at least a part of the off-gas mixture in a steam raising apparatus, producing steam of an elevated pressure; and
   (e) an expander for expanding the steam produced in step (d) for compressing the air or oxygen enriched air and/or the normally gaseous hydrocarbon feed used in step (a)

wherein there is no gas turbine installed in the plant.

2. An offshore platform which comprises the plant of claim 1.

* * * * *